United States Patent
Yang et al.

(10) Patent No.: US 11,925,705 B2
(45) Date of Patent: Mar. 12, 2024

(54) METHOD FOR CONTINUOUS FABRICATION OF MULTI-FUNCTIONAL NANOGELS

(71) Applicant: The Curators of the University of Missouri, Columbia, MO (US)

(72) Inventors: Hu Yang, Rolla, MO (US); Da Huang, Fuzhou (CN)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 17/947,058

(22) Filed: Sep. 16, 2022

(65) Prior Publication Data
US 2023/0080475 A1    Mar. 16, 2023

Related U.S. Application Data

(60) Provisional application No. 63/244,934, filed on Sep. 16, 2021.

(51) Int. Cl.
*A61K 9/06*      (2006.01)
*A61K 47/32*     (2006.01)
*A61K 47/36*     (2006.01)

(52) U.S. Cl.
CPC ............. *A61K 9/06* (2013.01); *A61K 47/32* (2013.01); *A61K 47/36* (2013.01)

(58) Field of Classification Search
None
See application file for complete search history.

(56) References Cited

U.S. PATENT DOCUMENTS

2017/0209386 A1*  7/2017  Pagels .................. A61K 9/5138

OTHER PUBLICATIONS

Markwalter & Prud'homme, Design of a Small-Scale Multi-Inlet Vortex Mixer for Scalable Nanoparticle Production and Application to the Encapsulation of Biologics by Inverse Flash NanoPrecipitation, J. Pharm. Sci., 107 (2018) pp. 2465-2471. (Year: 2018).*

Markwalter & Prud'homme, Design of a Small-Scale Multi-Inlet Vortex Mixer for Scalable Nanoparticle Production and Application to the Encapsulation of Biologics by Inverse Flash NanoPrecipitation, J. Pharm. Sci., 107 (2018) pp. 2465-2471, Supplemental Information. (Year: 2018).*

Tao et al., "Application of flash nanoprecipitation to fabricate poorly water-soluble drug nanoparticles," Acta Pharmaceutica Sinica B, 2019;9(1):4-18, https://doi.org/10.1016/j.apsb.2018.11.001, 15 pages.

(Continued)

*Primary Examiner* — Dominic Lazaro
(74) *Attorney, Agent, or Firm* — HOVEY WILLIAMS LLP

(57) ABSTRACT

Nanogels and methods of synthesizing and using these nanogels are provided. The nanogels are formed by mixing a building block (e.g., polymer), crosslinker, preferably a target (e.g., biomedical compound or molecule), and a solvent in a multi-inlet vortex mixer, so as to cause the polymer and crosslinker to react and form a chemically crosslinked polymer network. In embodiments including a target, the target will be interspersed in and among that network and can be physically embedded and/or chemically bound therein.

12 Claims, 13 Drawing Sheets

(56) References Cited

OTHER PUBLICATIONS

Markwalter et al., "Design of a Small-Scale Multi-Inlet Vortex Mixer for Scalable Nanoparticle Production and Application to the Encapsulation of Biologics by Inverse Flash NanoPrecipitation," Journal of Pharmaceutical Sciences, 107 (2018) 2465-2471, https://doi.org/10.1016/j.xphs.2018.05.003, 7 pages.

Gericke et al., "Nanoparticles Based on Hydrophobic Polysaccharide Derivatives—Formation Principles, Characterization Techniques, and Biomedical Applications," Macromolecular Bioscience, 2020, 20, 1900415, DOI: 10.1002/mabi.201900415, 39 pages.

Liu et al., "Mixing in a multi-inlet vortex mixer (MIVM) for flash nano-precipitation," Chemical Engineering Science, vol. 63, Issue 11, 2008, pp. 2829-2842, https://doi.org/10.1016/j.ces.2007.10.020, 14 pages.

Weng et al., "In Vitro Release Study of the Polymeric Drug Nanoparticles: Development and Validation of a Novel Method," Pharmaceutics 2020, 12, 732; doi: 10.3390/pharmaceutics12080732, 18 pages.

Maolin et al., "Bioorthogonal chemistry and illumination controlled programmed size-changeable nanomedicine for synergistic photodynamic and hypoxia-activated therapy," Biomaterials, vol. 284, May 2022, ISSN 0142-9612, https://doi.org/10.1016/j.biomaterials.2022.121480, pp. 1-8.

Li et al., "Efficient Light-Harvesting Systems with Tunable Emission through Controlled Precipitation in Confined Nanospace," Angew. Chem. Int. Ed. Engl., vol. 58, 2019, ISSN 61433-7851, https://doi.org/10.1002/anie.201812146. (1 page abstract attached).

Chow et al., "Assessment of the relative performance of a confined impinging jets mixer and a multi-inlet vortex mixer for curcumin nanoparticle production," European Journal of Pharmaceutics and Biopharmaceutics, vol. 88, Issue 2, 2014, pp. 462-471, doi: 10.1016/j.ejpb.2014.07.004. (1 page abstract attached).

\* cited by examiner

METHOD FOR CONTINUOUS FABRICATION OF MULTI-FUNCTIONAL NANOGELS

RELATED APPLICATIONS

The present application claims the priority benefit of U.S. Provisional Patent Application Ser. No. 63/244,934, filed Sep. 16, 2021, entitled METHOD FOR CONTINUATION FABRICATION OF MULTI-FUNCTIONAL NANOGELS, incorporated by reference in its entirety herein.

BACKGROUND

Field

The present disclosure is concerned with novel nanogels and methods of synthesizing these nanogels. The disclosure is also concerned with methods of using the nanogels in biomedical and/or pharmaceutical applications.

Description of Related Art

Over the last few decades, nanoparticle vehicles or "nanocarriers" have been developed for various applications, particularly biomedical applications (e.g., drug or gene delivery, bioimaging, biosensing, etc.). Several nanocarriers, however, suffer from poor stability in vivo, which leads to premature release of the "cargo" they are intended to deliver. Therefore, nanogels are particularly attractive because, in addition to the ability to protect the cargo from degradation and improve intracellular delivery and transfection efficiency, they are extremely stable in vivo due to their crosslinking nature. However, current preparation methods suffer drawbacks, including the significant involvement of organic solvents and/or surfactants, which makes purification difficult and gives rise to safety concerns. In addition, the successful industrialized production and clinical application of nanogels has long been limited by the lack of reproducible and scalable methods for preparation of uniform nanogels with good batch-to-batch consistency.

Thus, there is a need for a method, particularly an organic-solvent-free and/or solvent-free method, for scalable and continuous fabrication of nanogels.

SUMMARY

The present disclosure provides a water-based, continuous, nanogel generation platform utilizing a multi-inlet vortex mixer for scalable production of uniform and multi-functional nanogels. Broadly, a building block (e.g., reactive polymer), crosslinker, target (also referred to as a "payload," e.g., drug, gene, contrast agent, and/or protein), and optionally ligands and/or water are introduced into respective inlets of the multi-inlet vortex mixer. The four streams converge in the mixer, and the confined, impinging jet causes mixing of, and reaction between, the building block and the crosslinker, thus producing uniform nanogels in a continuous and reproducible way.

The disclosed process possesses several advantages. For example, continuous and reproducible preparation enables scale-up production of uniform nanogels in gram scale per day, overcoming the bottleneck of industrialized production. The invention further provides a versatile platform for preparation of various nanogels from different building blocks and crosslinkers. Multiple targets can be encapsulated in, or conjugated to, one nanogel to endow multifunctionality. Additionally, integration of other functional blocks, such as targeting ligands, is provided with this process. In one embodiment, water is the only solvent used in the process, which is a significant advantage over the prior art. That is, organic solvents are preferably avoided, thus avoiding organic solvent residues and the problems associated therewith. In other embodiments, surfactants are avoided, which is another significant advantage over the prior art.

In one embodiment, the disclosure provides a method of forming a loaded nanogel comprising micromixing a polymer, a crosslinker, a target, and a solvent system in a multi-inlet vortex mixer until the loaded nanogel is formed.

In another embodiment, the disclosure provides a method of forming a nanogel, with the method comprising creating a vortex comprising a polymer, a crosslinker, and a solvent system. The polymer and crosslinker react in the vortex to form a nanogel comprising a crosslinked polymer network.

A nanogel comprising a crosslinked polymer network is also provided. The crosslinked polymer network comprises:
 (i) a polyamidoamine dendrimer reacted with bis-(N-hydroxysuccinimide) functionalized thioketal, there being a target interspersed among the polymer network;
 (ii) a copper-decorated polyamidoamine dendrimer reacted with disulfide (N-hydroxysuccinimide); or
 (iii) both (i) and (ii).

BRIEF DESCRIPTION OF THE DRAWINGS

Figure (FIG.) 1A is a schematic representation (not to scale) of a continuous nanogel generation platform.

DETAILED DESCRIPTION

Figure 1A:
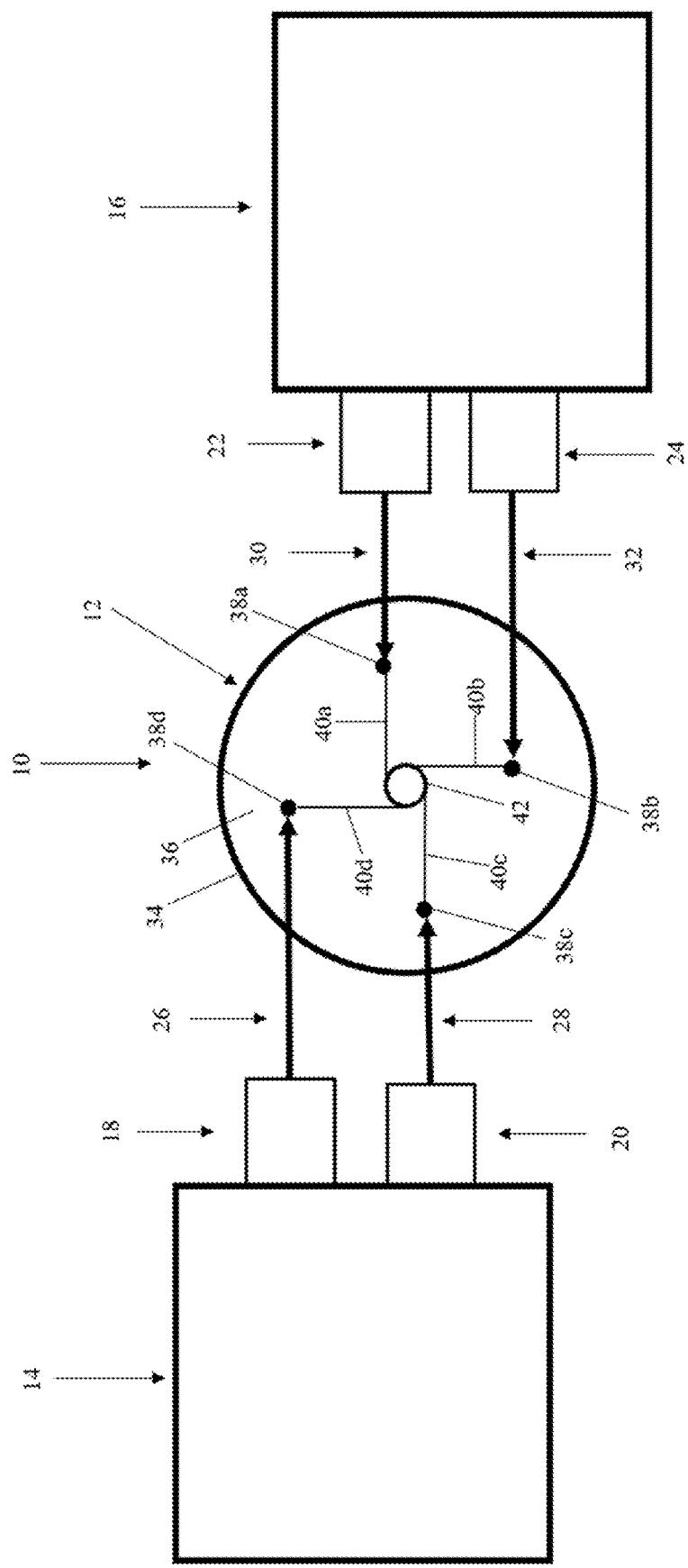
FIG. 1B is a schematic representation (not to scale) of a multi-inlet vortex mixer that can be used with the processes described herein.
FIG. 1C is a schematic representation (not to scale) of a multi-inlet vortex mixer comprising four inlets.
FIG. 1D is a photograph of a continuous nanogel generation platform described in Examples 2-8.

The present disclosure is concerned with novel nanogels and novel methods of synthesizing and using these nanogels.

Nanogel Components

Nanogels described herein are generally formed from a building block and a crosslinker selected to react with the building block so as to form the nanogel.

1. Building Block

Building blocks used to form the nanogels described herein comprise a polymer(s), oligomer(s), and/or monomer(s). Preferably, the building block comprises a polymer or a mixture of polymers.

In one embodiment, the polymer comprises recurring units that comprise at least one reactive group chosen from one or more of N-hydroxysuccinimide ("NHS"), sulfo-N-hydroxysuccinimide ("SNHS"), —NH$_2$, —NH—, thiol, methyl acrylate, methyl methacrylate, azide, alkyne, or combinations thereof.

Suitable polymers can be linear or branched. In some embodiments, the polymer comprises at least 2, preferably at least about 3, more preferably at least about 10, even more preferably at least about 15, and most preferably at least about 20 of these reactive groups per polymer. In another embodiment, the polymer comprises 2 to about 150, preferably 3 to about 125, more preferably 10 to about 100, and even more preferably 15 to about 50 reactive groups per polymer.

In some embodiments, the recurring units comprise at least 2 and more preferably at least 3 of these reactive groups per recurring unit. In other embodiments, the recurring unit comprises 1 to 3, and preferably 1 to 2 reactive groups per recurring unit.

These polymers can comprise, consist essentially of, or even consist of recurring units having the reactive group(s). In other embodiments, the polymer can be a copolymer of monomers comprising the reactive groups along with one or more other monomer types that lack the reactive groups. Regardless of the embodiment, at least about 50%, preferably about 75% to about 100%, more preferably about 90% to about 100%, and even more preferably about 100% (i.e., the polymer is a homopolymer) of the total recurring units will include a reactive group(s) at the ranges described previously.

In one embodiment, the branched polymer is a dendrimer. Suitable dendrimers include those that have at least about 16, preferably at least about 32, more preferably at least about 64, even more preferably at least about 128, and most preferably at least about 256 reactive groups at the dendrimer surface (referred to as "reactive surface groups"). In other embodiments, the dendrimer comprises about 16 to about 5,000, preferably about 32 to about 3,000, more preferably about 32 to about 2,000, even more preferably about 64 to about 1,000, and most preferably about 128 to about 1,000 reactive surface groups.

In some embodiments, the selected dendrimer(s) has an average hydrodynamic diameter of about 2.5 nm to about 11 nm, preferably about 3 nm to about 11 nm, more preferably about 4 nm to about 9 nm, even more preferably about 4.5 nm to about 8 nm, and most preferably about 5 nm to about 7 nm. Hydrodynamic diameter is typically determined by dynamic light scattering, as described in Example 3. The generation of the selected dendrimer can vary but is typically G2 to G10, preferably G3 to G8, more preferably G4 to G7, and even more preferably G5 to G6.

In some instances, the selected dendrimer comprises a metal-decorated dendrimer. The metal can be reacted or complexed with one or more groups on the dendrimer and/or physically entrapped within the branches of the dendrimer. Metal-decorated dendrimers can comprise a single metal, or a mixture of two or more metals can be present. Suitable metals include one or more of copper, gold, silver, platinum, cerium, cerium oxide, ferric oxide, or combinations thereof.

Polymers suitable for nanogel building blocks as described herein will typically have a weight average molecular weight ($M_w$) of about 300 Daltons to about 500,000 Daltons, preferably about 600 Daltons to about 500,000 Daltons, more preferably about 10,000 Daltons to about 500,000 Daltons, even more preferably about 20,000 Daltons to about 350,000 Daltons, and most preferably about 20,000 Daltons to about 200,000 Daltons, and/or a number average molecular weight ($M_n$) of about 150 Daltons to about 300,000 Daltons, preferably about 300 Daltons to about 300,000 Daltons, more preferably about 5,000 Daltons to about 300,000 Daltons, even more preferably about 10,000 Daltons to about 200,000 Daltons, and most preferably about 10,000 Daltons to about 100,000 Daltons. Molecular weight is measured by gel permeation chromatography ("GPC") according to ASTM D6474.

In embodiments where the polymer comprises a dendrimer, the weight average molecular weight is typically about 3,000 Daltons to about 500,000 Daltons, preferably about 10,000 Daltons to about 250,000 Daltons, more preferably about 15,000 Daltons to about 125,000 Daltons, and even more preferably about 20,000 Daltons to about 60,000.

Exemplary polymers suitable for use in the disclosed nanogel formation process include those chosen from one or more of polyamidoamine ("PAMAM") dendrimers, metal-decorated PAMAM (e.g., copper-decorated PAMAM, "PAMAM-Cu"), polyethylenimine (preferably branched), chitosan and its derivatives, amine-functionalized multi-armed polyethylene glycol (PEG), NHS functionalized hyaluronic acid ("HA-NHS"), sulfo-NHS functionalized hyaluronic acid ("HA-SNHS"), NETS functionalized multi-armed PEG, sulfo-NHS functionalized multi-armed PEG, NHS functionalized polyacrylic acid, sulfo-NHS functionalized polyacrylic acid, or combinations thereof.

2. Crosslinker

The crosslinker used to form the nanogels described herein can be selected depending on the particular polymer(s) being utilized. That is, the crosslinker is selected to be one that will form covalent bonds with the selected building block, and preferably with the reactive groups present on the building block.

In one embodiment, the crosslinker comprises a functional group that will covalently react with the reactive group(s) on the polymer(s). Examples of such functional groups include those chosen from one or more of NHS, SNHS, —NH$_2$, thiol, methyl acrylate, methyl methacrylate, azide, alkyne, or combinations thereof. Preferably, the crosslinker is multi-functional, and particularly di- or tri-functional. That is, the crosslinker preferably has at least 2, at least 3, or at least 4 functional groups per molecule of crosslinker. In some embodiments, the crosslinker will comprise 2 to 4, preferably 2 to 3, and preferably 2 functional groups per molecule of crosslinker.

In one embodiment, a preferred crosslinker comprises a polyamine, e.g., comprising 2 to 4, preferably 2 to 3, and more preferably 2 amino groups (i.e., diamine). In another embodiment, the crosslinker comprises poly(N-hydroxysuccinimide) functionalized crosslinker, with the latter preferably comprising 2 to 4, preferably 2 to 3, and more preferably 2 N-hydroxysuccinimide groups (i.e., a bis-(N-hydroxysuccinimide) functionalized crosslinker).

It will be appreciated that the crosslinker can be selected based on the application of the final nanogel. As a result, the crosslinker, in some embodiments, can be a non-degradable and/or stimuli-responsive crosslinker.

Examples of suitable crosslinkers for use herein include one or more of those chosen from bis-(N-hydroxysuccinimide) functionalized polyethylene glycols ("PEG-BN"), bis-amine functionalized polyethylene glycols ("PEG-BA"), bis-(N-hydroxysuccinimide) functionalized thioketal ("TK-BN"), 3,3'-Dithiodipropionic acid di(N-hydroxysuccinimide ester) (also referred to as "disulfide (N-hydroxysuccinimide) or "DSN" herein), cysteamine ("CA"), 3,3'-dithiodipropionic acid di(N-hydroxysuccinimide ester), cis-aconitic anhydride functionalized PEG, or combinations thereof. In some embodiments where the crosslinker comprises a bis-functionalized polyethylene glycol ("PEG"), the number of recurring ethylene glycol units typically comprises 2 to about 150, preferably 2 to about 125, and more preferably about 2 to about 100. In other embodiments where the crosslinker comprises a bis-functionalized polyethylene glycol ("PEG"), the number of recurring ethylene glycol units can comprise 2 to about 10, preferably 4 to about 9, and more preferably 5 to about 9.

3. Solvent

Solvent systems used to prepare the nanogels as described herein can comprises a single solvent or a mixture of two or more solvents. Depending on the embodiment, the solvent system comprises one or more solvents chosen from water, organic solvents, or mixtures thereof. Suitable organic solvents for use in the solvent system comprise those selected from the group of acetone, methanol, ethanol, tetrahydrofuran, dimethylsulfoxide, dimethylformamide, dioxane, and mixtures thereof.

In embodiments where the solvent system comprises a mixture of water and an organic solvent(s), the organic solvent(s) should be miscible with water. Preferably, the volume ratio of water to total organic solvent(s) in this embodiment is about 1:0.05 to about 1:3, more preferably about 1:0.1 to about 1:2, and even more preferably about 1:0.2 to about 1:1.

4. Target

In some embodiments, a target is introduced with other starting components during nanogel formation. The target can be, for example, any molecule, macromolecule, functional block, and/or drug that is desired to be present in the final nanogel. In embodiments where the target is for use in a biomedical application, the target can be, but is not limited to, one or more of a drug, gene, protein, plasmid, targeting ligand, contrast agent, or combinations thereof.

Depending on the selected target(s), the target can be physically encapsulated or chemically conjugated in the polymer network of the nanogel. In some embodiments where the target will be physically encapsulated within the nanogel, the target can undergo molecular interactions (e.g., hydrogen bonding) with the crosslinked polymer network of the nanogel. In other embodiments, no molecular interactions (or chemical reactions) will take place, but the target will simply be physically entrapped within the polymer network. Exemplary targets suitable for physical encapsulation include one or more of genes, proteins, plasmid, drugs without reactive groups, or combinations thereof.

In embodiments where the target is to be chemically conjugated within the nanogel, the target forms covalent bonds with the crosslinked polymer network of the nanogel. Exemplary targets for chemical conjugation include one or more of drugs with reactive groups.

It will be appreciated that, in some embodiments, the nanogel can comprise two, three, four, or five targets, which can endow multiple functions to the nanogel.

Nanogel Synthesis

1. Equipment

Referring to FIG. 1A, an exemplary continuous nanogel generation platform 10 is provided. Platform 10 comprises a micromixer 12 and syringe pumps 14, 16 operably connected to the micromixer 12. Each of syringe pumps 14, 16 comprises respective pairs of syringes 18, 20, and 22, 24. Each of syringes 18, 20, 22, 24 is operatively connected to respective tubing 26, 28, 30, 32.

Figure 1B:
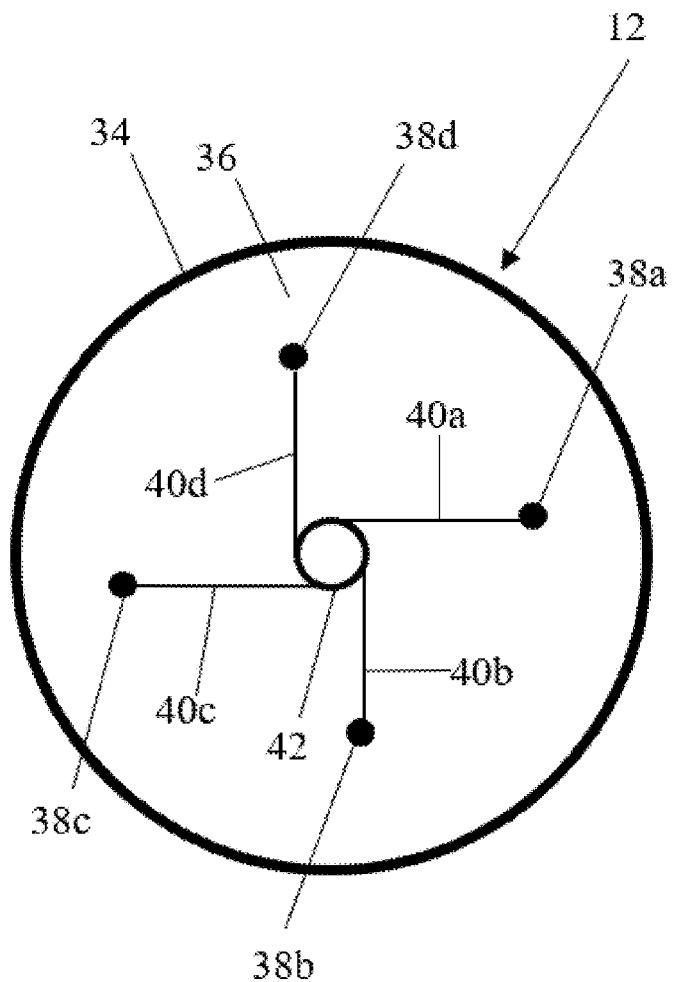

A preferred micromixer 12 is a multi-inlet vortex mixer. Referring to FIG. 1B, micromixer 12 generally comprises 2-3 separate components, with only the mixing component being shown here. That is, micromixer 12 comprises a generally discoid mixing body 34 presenting a substantially planar upper surface 36. Body 34 can be formed of any number of materials suitable for use in pharmaceutical manufacturing, including stainless steel or other inert material.

Upper surface 36 comprises inlets 38a-d, inlet channels 40a-d, and mixing chamber 42 formed therein. Each of inlets 38a-d is operably connected to respective tubing 26, 28, 30, 32 via respective inlet ports (not shown). Additionally, each inlet 38a-d is in (fluidic) communication with a respective inlet channel 40a-d. The inlet channels 40a-d are in (fluidic) communication with, and oriented tangentially to, mixing chamber 42. Mixing chamber 42 is generally circular in cross section and is operably connected to a reaction product outlet (not shown).

The respective sizes (e.g., diameters) and/or respective shapes of inlets 38a-d, inlet channels 40a-d, and/or mixing chamber 42 can be individually selected depending upon the desired reaction volume and/or desired flow patterns. For example, the inlet channels 40a-d can comprise an unpatterned surface (i.e., the surface is straight or smooth, or both). In some embodiments, the surfaces forming inlet channels 40a-d can comprise a herringbone or zigzag pattern. In use, one of the previously discussed separate components that is typically present in micromixer 12 is a top disk (not shown) removably fastened to body 34 so as to create a sealed reaction environment. This top disk typically houses the previously discussed inlet ports that are connected to tubing 26, 28, 30, 32.

2. Synthesis Process

Figure 1C:
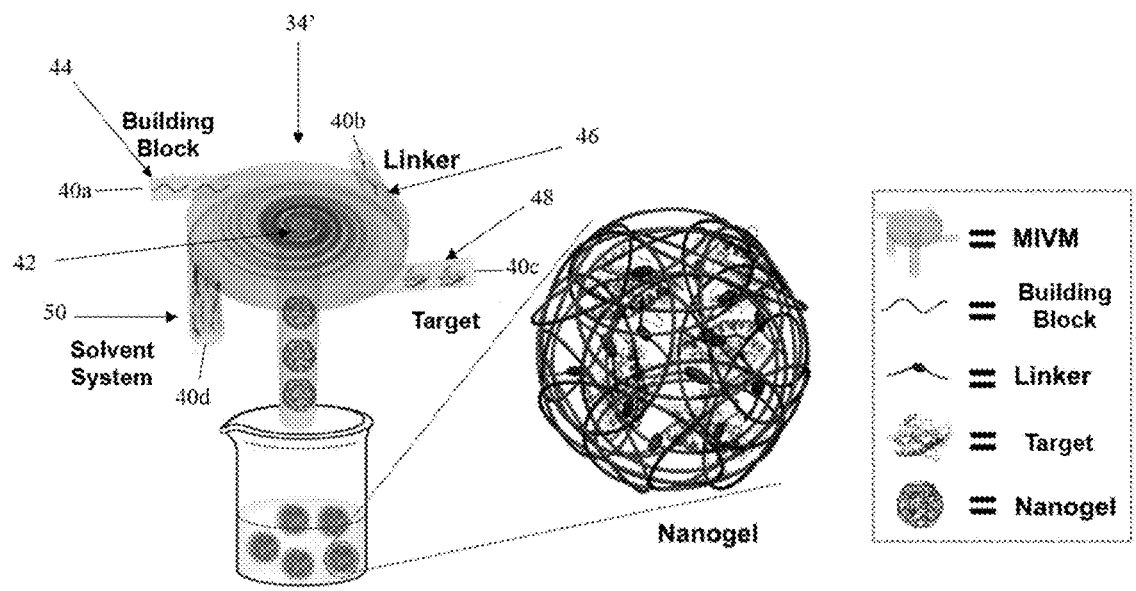
Figure 1D:
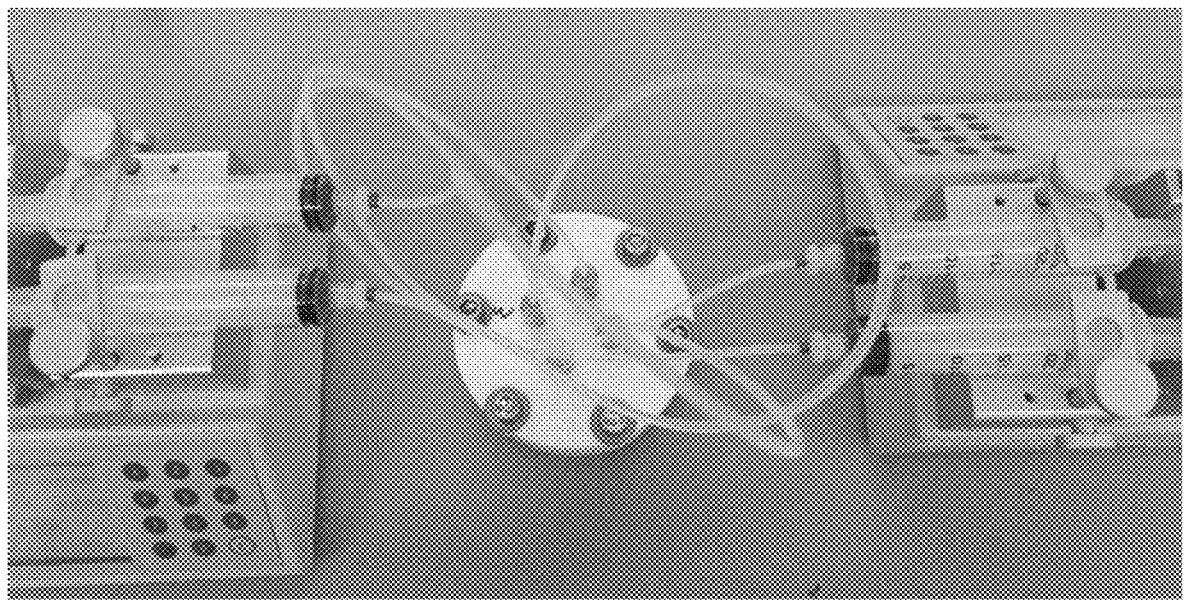

Generally, the synthesis process comprises continuous, turbulent micromixing of the building block, crosslinker, and target (if present) in a solvent system, under circular flow, until the nanogels are formed. FIG. 1C depicts this process schematically, where 34' is equivalent to the central region of previously described discoid mixing body 34 (i.e., the mixing chamber 42 and the portions of inlet channels 40*a-d* nearest mixing chamber 42).

A building block stream 44, a crosslinker stream 46, a target stream 48, and a solvent stream 50 are injected via the previously described syringe pumps 14, 16 and syringes 18, 20, 22, 24 into individual inlet ports of respective inlets 38*a-d* (as shown in FIG. 1B).

Building block stream 44 comprises a building block dissolved or dispersed in a solvent for the building block and is typically introduced into inlet 38*a* (and subsequently passed through inlet channel 40*a*). In one embodiment, the solvent for the building block comprises water at 90% by weight, preferably at least about 95% by weight, and more preferably at least about 100% by weight, based on the total weight of all solvents present in building block stream 44 taken as 100% by weight.

The building block is typically included in building block stream 44 at a concentration of about 0.1 mg/mL to about 100 mg/mL, preferably about 0.5 mg/mL to about 75 mg/mL, more preferably about 0.8 mg/mL to about 50 mg/mL, and even more preferably about 1 mg/mL to about 30 mg/mL. As used herein, when referring to stream concentrations, the term "mL" refers to the volume of solvent in which the building block, crosslinker, or target is dissolved or dispersed prior to introducing the building block stream, crosslinker stream, or target stream into the particular inlet 38*a-d*.

In one embodiment, building block stream 44 comprises at least about 90% by weight polymer(s), preferably at least about 95% by weight polymer(s), more preferably at least about 99% by weight polymer(s), and more preferably about 100% by weight polymer(s), based on the total weight of all non-solvents present in the building block stream 44 taken as 100% by weight. In addition to or alternatively, building block stream 44 comprises less than about 10% by weight monomers, preferably less than about 5% by weight monomers, more preferably less than about 3% by weight monomers, even more preferably less than about 1% by weight monomers, and most preferably about 0% by weight monomers, based on the total weight of all non-solvents present in the building block stream 44 taken as 100% by weight.

Crosslinker stream 46 comprises a crosslinker dissolved or dispersed in a solvent. In one embodiment, the solvent for the crosslinker comprises at least about 90% by weight water, preferably at least about 95% by weight water, and more preferably about 100% by weight, based on the total weight of all solvents present in crosslinker stream 46 taken as 100% by weight. In another embodiment, the solvent for the crosslinker comprises at least about 90% by weight acetone, preferably at least about 95% by weight acetone, and more preferably about 100% by weight acetone, based on the total weight of all solvents present in crosslinker stream 46 taken as 100% by weight.

The crosslinker stream 46 is typically introduced into inlet 38*b* (and subsequently passed through inlet channel 40*b*) such that the crosslinker is present at a concentration of about 0.1 mg/mL to about 100 mg/mL, preferably about 0.5 mg/mL to about 75 mg/mL, more preferably about 0.7 mg/mL to about 50 mg/mL, and even more preferably about 0.75 mg/mL to about 25 mg/mL.

Target stream 48 comprises a target dissolved or dispersed in a solvent. In one embodiment, the solvent for the target comprises at least about 90% by weight water, preferably at least about 95% by weight water, and more preferably about 100% by weight, based on the total weight of all solvents present in target stream 48 taken as 100% by weight. Depending on the target, it may be necessary to use DNAase-free water in target stream 48, as well as any other streams including water.

The target stream 48 is typically introduced into the inlet 38*c* (and subsequently passed through inlet channel 40*c*) such that the target is present at a concentration of about 0.01 mg/mL to about 1 mg/mL, preferably about 0.05 mg/mL to about 0.75 mg/mL, more preferably about 0.1 mg/mL to about 0.5 mg/mL, and even more preferably about 0.2 mg/mL to about 0.3 mg/mL.

In one embodiment, the molar ratio of total reactive groups in building block stream 44 to total crosslinker in crosslinker stream 46 is preferably about 1:0.1 to about 1:2, more preferably about 1:0.2 to about 1:1.5, and even more preferably about 1:0.5 to about 1:1. The weight ratio of total building block in building block stream 44 to total target in target stream 48 is preferably about 1:0.05 to about 1:2, more preferably about 1:0.05 to about 1:1.5, and even more preferably about 1:0.1 to about 1:1. The weight ratio of total crosslinker in crosslinker stream 46 to total target in target stream 48 is about 1:0.05 to about 1:2, preferably about 1:0.05 to about 1:1.5, and more preferably about 1:0.1 to about 1:1.

Solvent stream 50 comprises one or more solvents, as described previously. Table A sets forth ranges for various solvents that can be present (or not be present, as the case may be) in solvent stream 50. In other embodiments, the Table A ranges apply to the total solvents provided by the combination of streams 44, 46, 48, and 50, since each of these streams can contribute to the overall solvent system present during reaction. That is, the solvent system in which micromixing and nanogel formation take place can comprise the same solvent or a mixture of different solvents, depending on the solvents utilized in streams 44, 46, 48, and 50. Regardless of the embodiment, it is intended that the ranges in each of Rows 1-5 can be combined with any one or more of the ranges in Rows 1-5, to the extent that combination is not contradictory.

TABLE A

| | Component | % by Weight* | % by Weight* | % by Weight* | % by Weight* |
|---|---|---|---|---|---|
| 1 | Water | at least about 90% | at least about 95% | at least about 98% | about 100% |
| 2 | Organic Solvents | less than about 5% | less than about 3% | less than about 1% | about 0% |
| 3 | Acetone** | at least about 90% | at least about 95% | at least about 98% | about 100% |
| 4 | Acetone*** | about 25% to about 75% | about 40% to about 60% | about 45% to about 55% | about 50% |
| 5 | Organic Solvents Other than Acetone | less than about 5% | less than about 3% | less than about 1% | about 0% |

*% by weight based on the total weight of all solvents taken as 100% by weight.
**Ranges apply individually to streams 44, 46, 48, and/or 50 only and not to the overall solvent system in mixing chamber 42.
***Ranges apply to acetone in overall solvent system in mixing chamber 42.

In some embodiments, the solvent system in which micromixing and nanogel formation take place comprises a mixture of water and an organic solvent(s). In such embodiments, the volume ratio of water to total organic solvent(s) is preferably about 1:0.05 to about 1:3, more preferably about 1:0.1 to about 1:2, and even more preferably about 1:0.2 to about 1:1.

Two, three, or all four of streams 44, 46, 48, and 50 can be introduced into individual inlet ports of respective inlets 38a-d at the same (or substantially the same) injection rate. In other embodiments, two, three, or all four of streams 44, 46, 48, and 50 are introduced at different injection rates. Regardless of whether these injection rates are the same or different, they can be varied between injection rate and/or flow rates of about 1 mL/min to about 100 mL/min, preferably about 5 mL/min to about 80 mL/min, more preferably about 10 mL/min to about 60 mL/min, and even more preferably about 20 mL/min to about 50 mL/min. In one embodiment, the streams 44, 46, 48, and 50 are independently introduced at the same, or substantially the same, injection rate and/or flow rate. "Substantially the same" refers to a variation of about 2 mL/min or less, preferably about 1 mL/min or less, and even more preferably about 0.2 mL/min.

Regardless of the concentrations or injection/flow rates, streams 44, 46, 48, and 50 flow through respective inlet channels 40a-d to mixing chamber 42. As described previously, the inlet channels 40a-d are positioned tangentially relative to mixing chamber 42. As a result, streams 44, 46, 48, and 50 enter into mixing chamber 42 in a tangential manner, creating a circular flow or vortex within mixing chamber 42. Mixing is typically carried out for a time period of about 15 seconds to about 60 minutes, preferably about 30 seconds to about 45 minutes, and more preferably about 1 minute to about 10 minutes. Preferably, one, two, or all three of the injection, flow, or mixing are carried out at ambient temperatures (e.g., 20-25° C.).

Advantageously, the confined impinging and/or turbulent, circular mixing of the streams 44, 46, 48, and 50 effects the mixing of, and reaction between, the building block and crosslinker to form uniform nanogels in a continuous and reproducible manner. That is, the building block and crosslinker react with one another, preferably forming covalent bonds, thereby yielding a chemically-crosslinked nanogel. Additionally, the target will preferably become either physically embedded within the crosslinked polymer network and/or chemically bonded to components of the network, as described previously. It will be appreciated that in embodiments where the building block primarily or entirely comprises a polymer, little to no polymerization takes place in the mixing chamber 42, which can allow a more dense crosslinked network to be formed and/or higher target loading to be achieved.

Following the disclosed processes result in nanogels being formed at a rate of at least about 5 grams per day, preferably at least about 10 grams per day, more preferably at least about 50 grams per day, and even more preferably at least about 100 grams per day. In embodiments where an organic solvent that is miscible with water is used, the nanogels can be dried in a rotatory evaporator, preferably at a temperature of about 15° C. to about 25° C. and pressure of about 5 MPa to about −5 MPa, for a time period of about 30 seconds to about 30 minutes.

Advantageously, the synthesis process can form nanogels without crystallization. That is, the above-described mixing does not create supersaturation conditions that trigger and/or favor nucleation. As a result, the nanogels do not precipitate from solution nor are they forced out of solution by an anti-solvent and thus, do not require stabilization with an emulsifying agent (and preferably not with any other type of surfactant either). Thus, in some embodiments, an anti-solvent(s) and/or an emulsifying agent(s) are not used during the synthesis process. That is, the total amount of anti-solvent in streams 44, 46, 48, and 50 combined is less than about 5% by weight, preferably less than about 3% by weight, more preferably less than about 1% by weight, and even more preferably about 0% by weight, and/or the total amount of emulsifying agent (and preferably the total amount of all types of surfactants) in streams 44, 46, 48, and 50 combined is less than about 5% by weight, preferably less than about 3% by weight, more preferably less than about 1% by weight, and even more preferably about 0% by weight. The foregoing anti-solvent ranges apply to anti-solvents for one, two, three, or four of the building block, crosslinker, target, and/or formed nanogel.

It will be appreciated that the above process can be varied in a number of ways. For example, FIGS. 1A-1C depict a micromixer 12 with four inlets 38a-d (and correspondingly four inlet channels 40a-d). It will be appreciated that this number can varied to be two, three, five, six, or even seven, provided the tangential arrangement is still achieved. Additionally, multiple platforms could be utilized to scale up the process, and/or multiple micromixers 12 can be connected within the same system to scale up the process.

Other potential variations of the above process relate to the streams. For example, FIGS. 1A-1C depict the use of a target stream 48. However, a target stream 48 is only required in instances where the formation of a loaded nanogel is desired. In other instances, a target stream 48 could be omitted, in which case a non-loaded nanogel (i.e., one lacking a target) can be formed.

In another stream variation, a separate solvent stream 50 need not be utilized. That is, the solvent system in the mixing chamber 42 can be entirely supplied by the solvents used to carry the building block, crosslinker, and target (if present). In such instances, the ranges of Table A would still apply to these embodiments, and again, the ranges in each of Rows 1-5 can be combined with any one or more of the ranges in Rows 1-5, to the extent that combination is not contradictory.

Additionally, stream positioning can be altered. For example, there could be two building block streams 44 and/or two crosslinker streams 46. Similar streams can be positioned adjacent or opposite one another. Additionally, the two building block streams 44 could comprise the same or different building block types and/or quantities, and/or the two crosslinker streams 46 could comprise the same or different crosslinker types and/or quantities.

Nanogel Chemical Composition

1. Non-Loaded Nanogels

In some embodiments, the non-loaded nanogel comprises, consists essentially of, and/or consists of the building block(s) crosslinked with the crosslinker(s). In other embodiments, the non-loaded nanogel comprises, consists essentially of, or consists of the building block(s) crosslinked with the crosslinker(s), and the solvent(s).

2. Loaded Nanogels

In some embodiments, the loaded nanogel comprises, consists essentially of, and/or consists of the building block(s) crosslinked with the crosslinker(s), and the target(s) interspersed in and/or among the crosslinked building block(s) and crosslinker(s). In other embodiments, the loaded nanogel comprises, consists essentially of, and/or consists of the building block(s) crosslinked with the crosslinker(s), the target(s) interspersed in and/or among the crosslinked building block(s) and crosslinker(s), and the solvent(s).

The weight ratio of total building block to total target in the loaded nanogel is preferably about 1:0.05 to about 1:2, more preferably about 1:0.05 to about 1:1.5, and even more preferably about 1:0.1 to about 1:1. The weight ratio of total crosslinker to total target in the loaded nanogel is preferably about 1:0.05 to about 1:2, more preferably about 1:0.05 to about 1:1.5, and even more preferably about 1:0.1 to about 1:1. It will be appreciated that some or all of the reactive groups and/or crosslinker will be "reacted" reactive groups and "reacted" crosslinker, depending on the degree of crosslinking that took place. The ratios of this paragraph are intended to encompass both reacted and unreacted.

3. Both Loaded and Non-Loaded Nanogels

The molar ratio of total building block reactive groups to total crosslinker in the nanogel is preferably about 1:0.1 to about 1:2, more preferably about 1:0.2 to about 1:1.5, and even more preferably about 1:0.5 to about 1:1. Again, some or all of the reactive groups and/or crosslinker will be "reacted" reactive groups and "reacted" crosslinker, depending on the degree of crosslinking that took place, and the ratios of this paragraph are intended to encompass both reacted and unreacted.

In some embodiments, the total weight of emulsifying agents (and preferably of all types of surfactants) in the nanogel comprises less than about 5% by weight, preferably less than about 3% by weight, more preferably less than about 1% by weight, and even more preferably about 0% by weight, based upon the total weight of the nanogel taken as 100% by weight. Additionally or alternative, the total weight of anti-solvents in the nanogel comprises less than about 5% by weight, preferably less than about 3% by weight, more preferably less than about 1% by weight, and even more preferably about 0% by weight, based upon the total weight of the nanogel taken as 100% by weight.

Furthermore, in some embodiments, the nanogels will comprise solvent levels as previously disclosed in Table A. Again, it is intended that the ranges in each of Rows 1-5 can be combined with any one or more of the ranges in Rows 1-5, to the extent that combination is not contradictory.

Nanogel Properties

By choosing different building blocks and crosslinkers, and by controlling the injection rate and ratio of building blocks to crosslinkers, the synthesis process can form nanogels of varying sizes, crosslinking densities, responsiveness, and/or surface charges.

Depending on the building block selected, the nanogels have an average hydrodynamic size (determined as described in Example 3) of about 10 nm to about 1,000 nm, preferably about 25 nm to about 750 nm, and more preferably about 50 nm to about 500 nm, and/or have a polydispersity index (determined by dynamic light scattering) of less than about 0.35, preferably less than about 0.25, more preferably less than about 0.15, and most preferably less than about 0.1. Depending on the crosslinker used, the nanogel can be a non-responsive nanogel or a stimuli-responsive nanogel.

Furthermore, the nanogels each possess unique electrical properties. In embodiments where the nanogel is a non-loaded nanogel, depending on the building block selected, the non-loaded nanogel can be positively- or negatively-charged. For example, a positively-charged nanogel comprises a building block having two or more $-NH_2$ moieties and/or a zeta potential of about 5 mV to about 50 mV, preferably about 10 mV to about 45 mV, more preferably about 15 mV to about 40 mV, and even more preferably about 20 mV to about 35 mV. A negatively-charged nanogel comprises a building block having two or more NHS and/or SNHS moieties, and/or a zeta potential of about −5 mV to about −50 mV, preferably about −10 mV to about −45 mV, more preferably about −15 mV to about −40 mV, and even more preferably about −20 mV to about −35 mV.

In embodiments where the nanogel is a loaded nanogel, the target(s) can also contribute to the overall charge of the loaded nanogel. In these embodiments, the loaded nanogel has a zeta potential of about −150 mV to about 150 mV, preferably about −100 mV to about 100 mV, more preferably about −50 mV to about 50 mV, and even more preferably about −10 mV to about 10 mV. In other embodiments, the loaded nanogel has a zeta potential of about 900 mV to about 1,000 mV.

Methods of Using the Nanogels

Though the above-described nanogels can be used in many applications (e.g., sensors, thermometers), the nanogels are preferably used in a biomedical and/or pharmaceutical application. Due to their ability to respond to external stimuli (e.g., pH changes, temperature, magnetic field, ionic strength), the loaded nanogels can deliver active molecules, macromolecules, functional blocks, and/or drugs to desired areas of the human body, thus treating cancers, central nervous system diseases, cardiovascular diseases, autoimmune diseases, neurodegenerative disorders, diabetes, and/or inflammatory disorders. Additionally, the loaded nanogels can be used for imaging (e.g., magnetic resonance imaging, positron emission tomography imaging, fluorescence-based optical imaging), diagnostics, and/or regenerative medicine (e.g., wound healing, tissue regeneration) applications.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10"

(with no upper bounds) and a claim reciting "less than about 100" (with no lower bounds).

EXAMPLES

The following examples set forth methods in accordance with the disclosure. It is to be understood, however, that these examples are provided by way of illustration and nothing therein should be taken as a limitation upon the overall scope.

Example 1

Materials

The materials used in the following Examples were obtained from the sources described in this paragraph. Polyamidoamine dendrimer—Generation 5 with a 1,4-diaminobutane core ("PAMAM G5") was purchased from NanoSynthons LLC (Mt. Pleasant, MI), and sulfo-N-hydroxysuccinimide functionalized hyaluronic acid (HA-SNHS) and copper-decorated PAMAM (PAMAM-Cu) were synthesized in the lab using published methods. Bis-NHS functionalized polyethylene glycol (sold under the name Bis(HNS)PEG5; PEG-BN) and cysteamine (CA) were obtained from Sigma-Aldrich Co. (St. Louis, MO).

Bis-NHS functionalized thioketal (TK-BN) was synthesized as described by Maolin et al., Bioorthogonal chemistry and illumination controlled programmed size-changeable nanomedicine for synergistic photodynamic and hypoxia-activated therapy, Biomaterials, Vol. 284, 2022, ISSN 0142-9612, https://doi.org/10.1016/j.biomaterials.2022.121480, incorporated by reference herein. Disulfide-NHS (DSN) was synthesized as described by Li et al., Efficient Light-Harvesting Systems with Tunable Emission through Controlled Precipitation in Confined Nanospace, Angew. Chem. Int. Ed., Vol. 58, 2019, ISSN 61433-7851, https://doi.org/10.1002/anie.201812146, incorporated by reference herein.

Acetone was purchased from Fisher Scientific (Waltham, MA), and deionized (DI) water was used. Glutathione (GSH) was purchased from Sigma-Aldrich Co. (St. Louis, MO), and pZsGreen1-C1 plasmid was obtained from Takara Bio USA, Inc. (San Jose, CA). All the reagents and solvents were used as received.

Example 2

1. Continuous Nanogel Generation Platform

To address the poor batch-to-batch consistency and difficulty in scale-up preparation of the traditional methods for nanogel ("NG") fabrication, a continuous nanogel generation platform for scalable production of uniform and multifunctional NGs was prepared. As shown in FIG. 1A, the prototype of the continuous nanogel generation platform comprised syringe pumps (Fusion 200 Two-Channel Syringe Pump, obtained from Chemyx, Inc.) and a multi-inlet vortex mixer as described by Chow et al., "Assessment of the relative performance of a confined impinging jets mixer and a multi-inlet vortex mixer for curcumin nanoparticle production," European Journal of Pharmaceutics and Biopharmaceutics, Volume 88, Issue 2, 2014, pages 462-471, incorporated by reference herein.

The multi-inlet vortex mixer included four inlets and a small chamber for introducing and mixing different components and payloads to form the NGs. The pumps were used to vary the mixing rate, and thereby control the size of the NGs. Typically, reactive polymers as building blocks were introduced at one inlet of the multi-inlet vortex mixer, whole crosslinkers (also referred to as "linkers") and the payload (drug, gene, and/or protein) we separately introduced at other inlets. In some instances, ligands or water were introduced at the fourth inlet. The streams converged in the mixing chamber of the mixer, and the confined impinging jet effected mixing of, and reaction between, the polymer and the crosslinker to produce uniform NGs in a continuous and reproducible way (see schematic illustration in FIG. 1B).

2. General Synthesis Method Using a Continuous Nanogel Generation Platform

Figure 2:
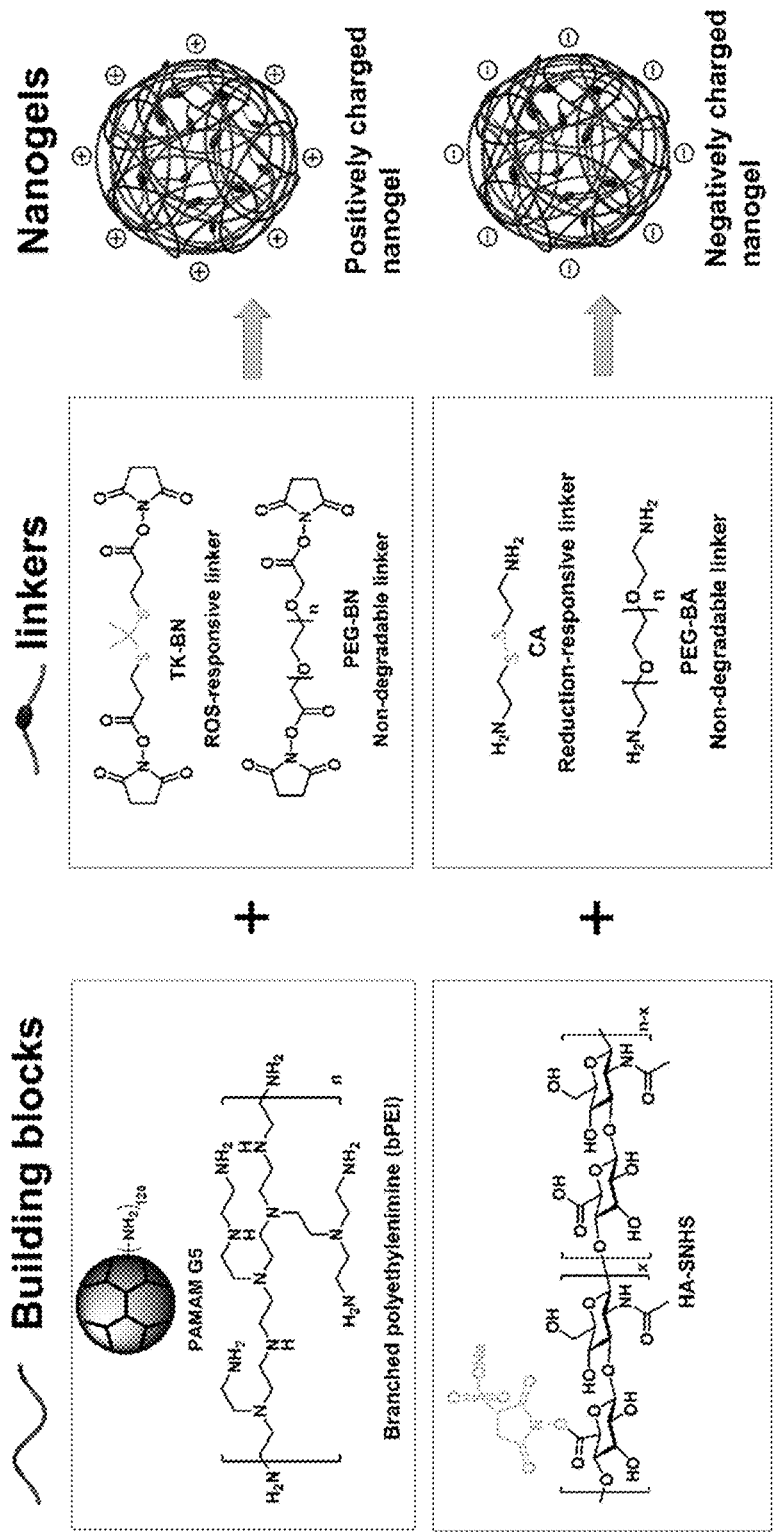
FIG. 2 is a schematic representation of positively- or negatively-charged nanogels formed using different building blocks and crosslinkers (Example 2)

Using a continuous nanogel generation platform, a series of NGs with different structures and properties were fabricated. As demonstrated in FIG. 2, different reactive polymers (also referred to as building blocks), such as PAMAM dendrimers, branched polyethylenimine, and HA-SNHS can be chosen as building blocks due to the different charges, commercial availability, and/or ease of preparation. Additionally, different linkers, such as non-degradable linkers (e.g., PEG-BN and/or bis-amine functionalized PEG) and stimuli-responsive linkers (e.g., TK-BN and/or CA) can be used to crosslink these polymers to form NGs.

The building blocks was dissolved in water or buffers with a concentration of 0.1~100 mg/mL, and then introduced into two inlets that are preferably adjacent one another. The crosslinkers were also dissolved in solvents that were mixable with water, and the concentrations thereof were adjusted to control the crosslinking density (usually in the range of 0.01~100 mg/mL). The crosslinker solution was introduced into the other two inlets. Subsequently, these solutions were mixed at injection rates of 1-100 mL/min, and NGs are yielded. By choosing different building blocks and crosslinkers, and by controlling the injection rate and ratio of building blocks to crosslinkers, various NGs with different sizes, crosslinking densities, surface charges, and/or responsiveness could be obtained for delivery of target payloads with different characteristics on demand.

Example 3

Fabrication of PAMAM/TK-BN NGs

1. Method

Figure 3A:
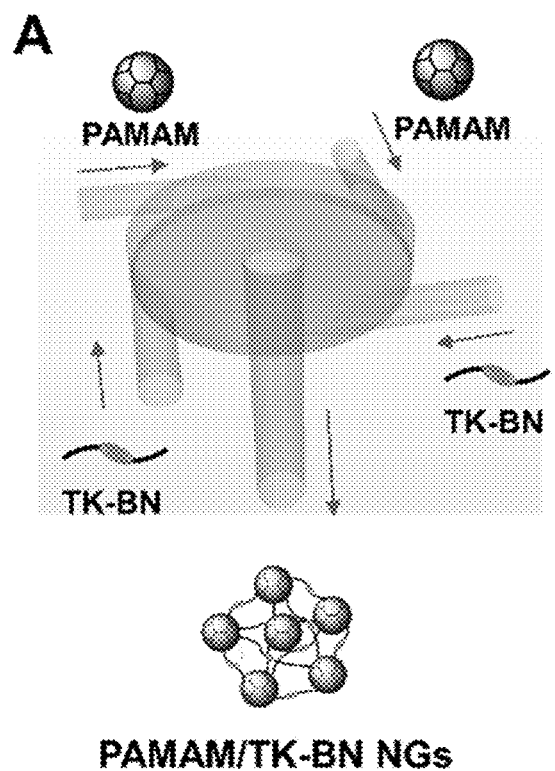
FIG. 3A is a schematic representation of a process using a multi-inlet vortex mixer to form PAMAM/TK-BN nanogels as described in Example 3.

PAMAM G5 was dissolved in water by stirring at room temperature, forming a first solution having a concentration of 1 mg/mL. Then, TK-BN was dissolved in acetone by mixing and shaking at room temperature, forming a second solution having a concentration of 0.75 mg/mL. The two solutions were loaded into syringes. Then, the syringes, charged with PAMAM and TK-BN, were each separately connected to two inlets of the multi-inlet vortex mixer (see FIG. 3A). A separate solvent stream was not used. Subsequently, these solutions were mixed at an injection rate of 40 mL/min using the syringe pump. After 1 minute, the received solution was rotary evaporated at room temperature and −0.08 MPa for 10 minutes using a Hei-VAP Core rotary evaporator (Heidolph NA LLC, Germany) to remove acetone, yielding the PAMAM/TK-BN NGs.

2. Results

The following instruments were used to physically characterize the PAMAM/TK-BN NGs prepared according to the method described in Part 1 of this Example. Transmission electron microscopy (TEM) was conducted using a JEM-1400 (JEOL, Japan) microscope. The average hydrodynamic size of the NGs was determined by dynamic light scattering (DLS) using a Zetasizer Lab (Malvern Panalytical, UK) instrument, and the polydispersity index of the NGs was determined using a Zetasizer Lab (Malvern Panalytical, UK) instrument. The zeta potential of the NGs was determined using a Zetasizer Lab (Malvern Panalytical, UK) instrument. The size distribution was measured using a Zetasizer Lab (Malvern Panalytical, UK) instrument and graphed using Graphpad Prism 8.0 software.

Figure 3B:
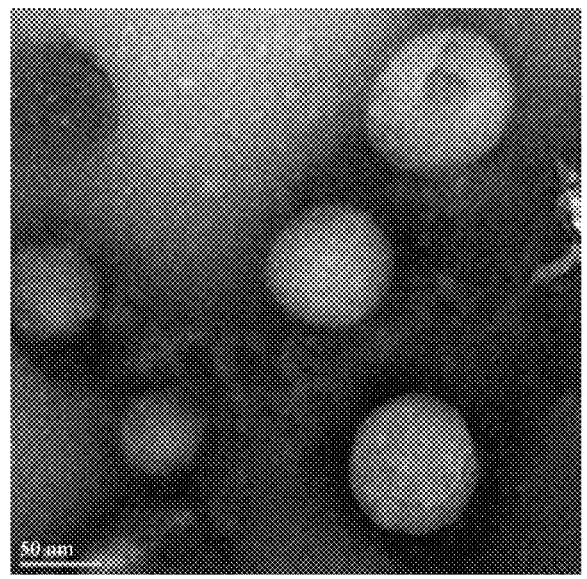
FIG. 3B is a scanning electron microscopy (SEM) photograph of the PAMAM/TK-BN nanogels formed as described in Example 3.
Figure 3C:
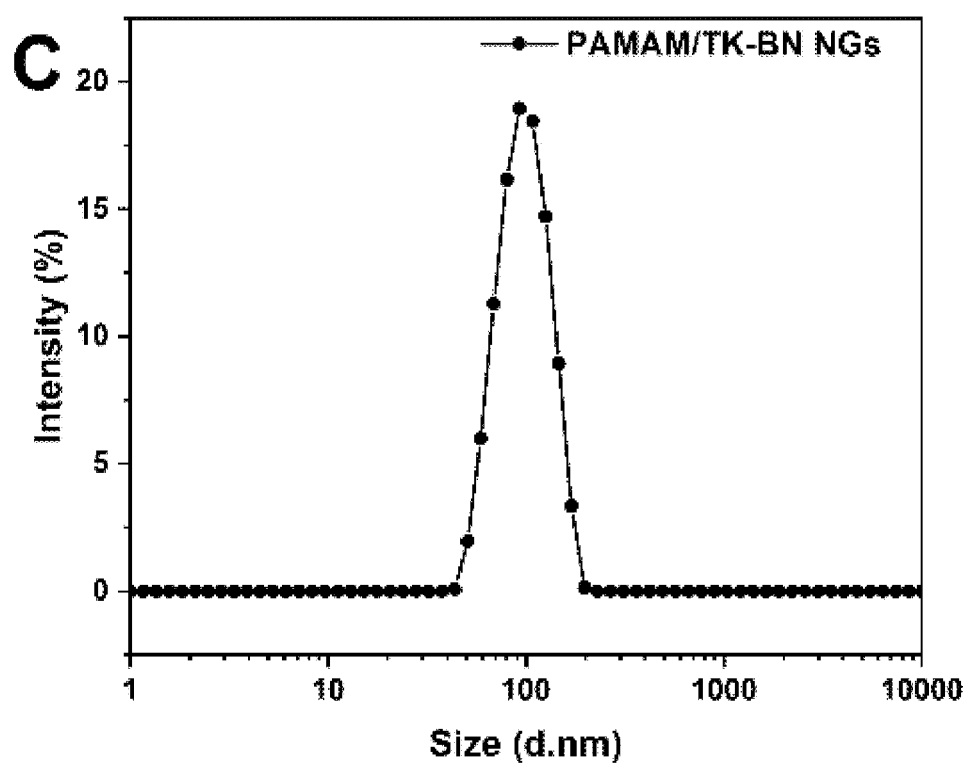
FIG. 3C is a graph showing the average hydrodynamic size distribution data determined by dynamic light scattering ("DLS") for the PAMAM/TK-BN nanogels of Example 3.

As illustrated in FIG. 3B, the TEM image of the PAMAM/TK-BNNGs indicated they were spherical particles with a size of about 50-100 nm. The average hydrodynamic size was 102 nm (see FIG. 3C), and the size distribution was narrow with a low polydispersity index (PDI) of 0.299, indicating good uniformity of the NGs (see Table 1). The PAMAM/TK-BN NGs were positively charged due to the positively charged PAMAM, which was proved by the zeta potential of 24.13±0.93 mV (see Table 1).

TABLE 1

Properties of PAMAM/TK-BN NGs

| Samples | Average Size (nm) | PDI | Zeta Potential (mV) |
| --- | --- | --- | --- |
| PAMAM/TK-BN NGs | 102 | 0.299 | 24.13 ± 0.93 |

Example 4

Fabrication of PAMAM/PEG-BN NGs

1. Method

Figure 4A:
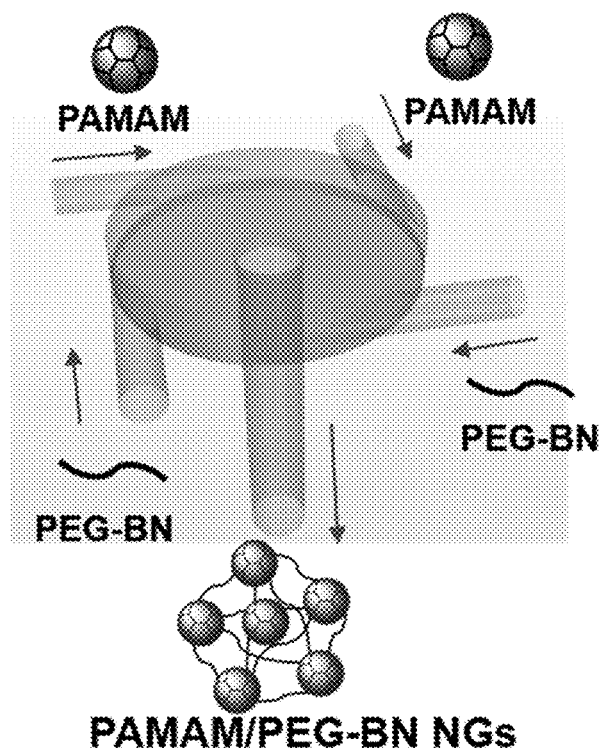
FIG. 4A is a schematic representation of a multi-inlet vortex mixer forming PAMAM/PEG-BN nanogels as described in Example 4.

PAMAM G5 was dissolved in water by stirring at room temperature, forming a first solution having a concentration of 1 mg/mL. Then, PEG-BN was dissolved in water by mixing and shaking at room temperature, forming a second solution having a concentration of 1.1 mg/mL. The two solutions were loaded to syringes, and the syringes, charged with PAMAM G5 and PEG-BN, were each separately connected to two inlets of the multi-inlet vortex mixer (FIG. 4A). A separate solvent stream was not used. Subsequently, these solutions were mixed at an injection rate of 40 mL/min using the syringe pump. The received solution was set for 1 minute, yielding the PAMAM/PEG-BN NGs.

2. Results

Figure 4B:
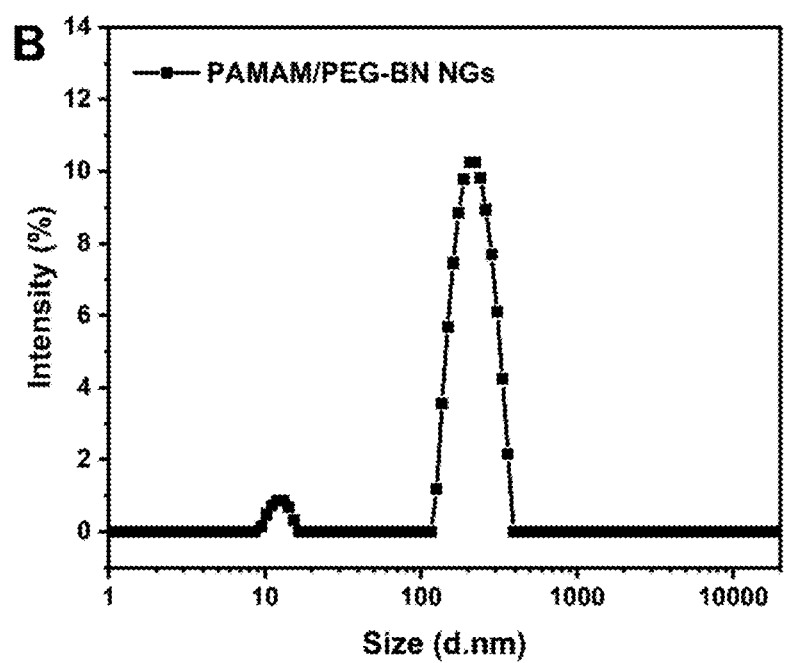
FIG. 4B is a graph showing the average hydrodynamic size distribution data determined by DLS for the PAMAM/PEG-BN nanogels formed in Example 4.

The same instruments described in Part 2 of Example 3 were used to physically characterize the PAMAM/PEG-BN NGs prepared in Part 1 of this Example. The size distribution of the PAMAM/PEG-BN NGs was quite narrow, although a small peak attributed to small particles was observed (FIG. 4B). The average hydrodynamic size determined by DLS was 223 nm with a PDI of 0.173, indicating uniform NGs were obtained (see Table 2). The zeta potential of the PAMAM/PEG-BN NGs was 32.35±1.34 mV (see Table 2), which was due to the use of the positively charged PAMAM.

TABLE 2

Properties of PAMAM/PEG-BN NGs

| Samples | Average Size (nm) | PDI | Zeta Potential (mV) |
| --- | --- | --- | --- |
| PAMAM/PEG-BN NGs | 223 | 0.173 | 32.35 ± 1.34 mV |

Example 5

Fabrication of HA-SNHS/CA NGs

1. Method

Figure 5A:
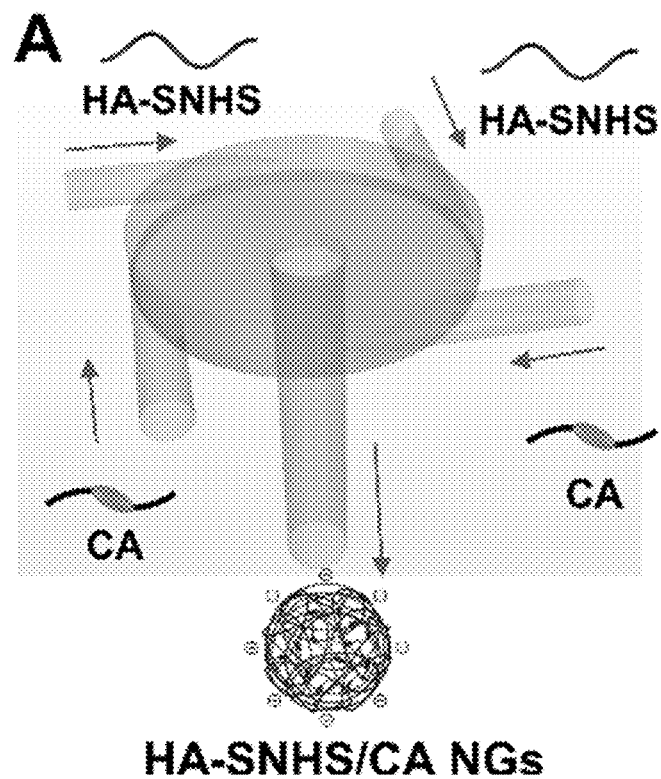
FIG. 5A is a schematic representation of a multi-inlet vortex mixer forming HA-SNHS/CA nanogels (Example 5)

HA-SNHS was dissolved in water by stirring at room temperature for a few minutes, forming a first solution having a concentration of 1 mg/mL. CA was separately dissolved in water by mixing and shaking at room temperature, forming a second solution having a concentration of 0.25 mg/mL. The two solutions were loaded into syringes, and the syringes charged with HA-SNHS and CA were each separately connected to two inlets of the multi-inlet vortex mixer (FIG. 5A). A separate solvent stream was not used. Subsequently, these solutions were mixed at an injection rate of 40 mL/min using the syringe pump. The received solution was set for 1 minute, yielding the HA-SNHS/CA NGs.

2. Results

Figure 5B:
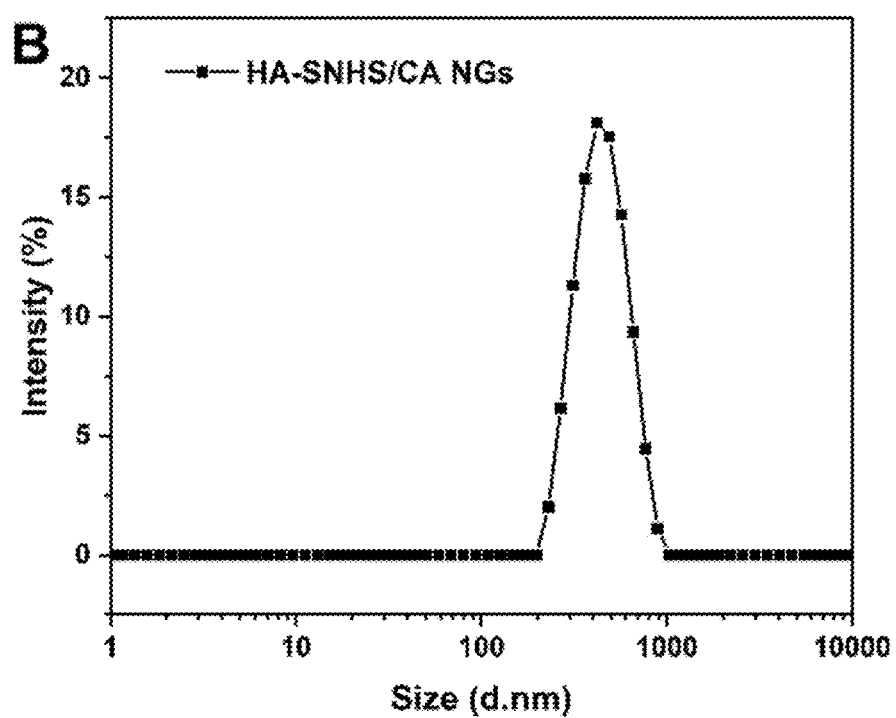
FIG. 5B is a graph showing the average hydrodynamic size distribution data determined by DLS for the HA-SNHS/CA nanogels formed in Example 5.

The same instruments described in Part 2 of Example 3 were used to physically characterize the HA-SNHS/CA NGs prepared in Part 1 of this Example. The size distribution of the HA-SNHS/CANGs was narrow (FIG. 5B). The average hydrodynamic size determined by DLS was 426 nm with a PDI of 0.017 (see Table 3), indicating uniform NGs were obtained. The zeta potential of the HA-SNHS/CA NGs was −22.53±1.92 mV (see Table 3), which was due to the negatively charged HA-SNHS that was utilized.

TABLE 3

Properties of HA-SNHS/CA NGs

| Samples | Average Size (nm) | PDI | Zeta Potential (mV) |
| --- | --- | --- | --- |
| HA-SNHS/CA NGs | 426 | 0.017 | −22.53 ± 1.92 mV |

Example 6

Fabrication of Drug-Loaded PAMAM/TK-BN NGs

1. Method

Figure 6A:
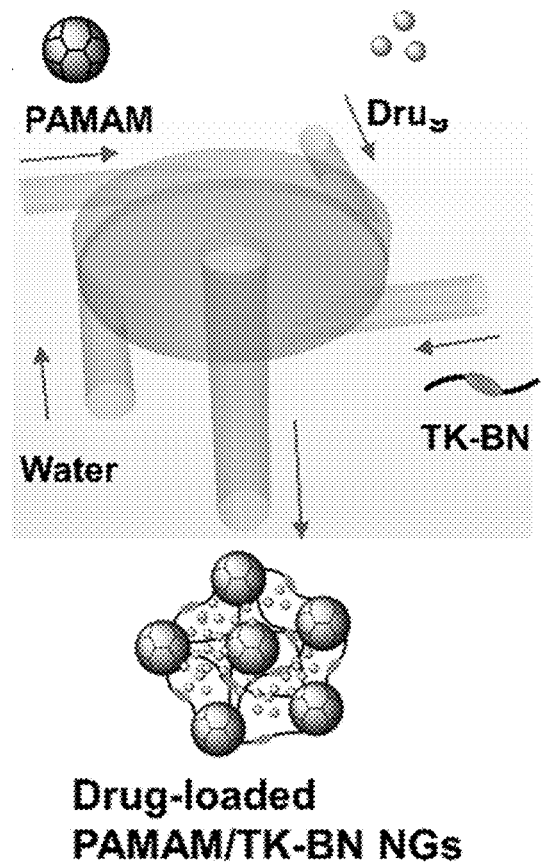
FIG. 6A is a schematic representation of a multi-inlet vortex mixer forming drug-loaded PAMAM/TK-BN nanogels as described in Example 6.

PAMAM G5 was dissolved in water by stirring at room temperature, forming a first solution having a concentration of 1 mg/mL. Then, TK-BN was dissolved in acetone by mixing and shaking at room temperature, forming a second solution having a concentration of 0.75 mg/mL. GSH as a model drug (i.e., the target payload) was dissolved in water, forming a third solution having a concentration of 0.2 mg/mL. These three solutions were loaded into respective syringes, and the syringes were connected to respective inlets of the multi-inlet vortex mixer as shown in FIG. 6A. The fourth inlet was connected to a syringe containing water for injecting the solvent stream. Subsequently, these solutions were mixed at an injection rate of 40 mL/min using the syringe pump. After being set for 1 minute, the received solution was rotary evaporated at room temperature and −0.08 MPa for 10 minutes using a Hei-VAP Core rotary evaporator (Heidolph NA LLC, Germany) to remove acetone, yielding plasmid-loaded PAMAM/TK-BN NGs.

2. Results

Figure 6B:
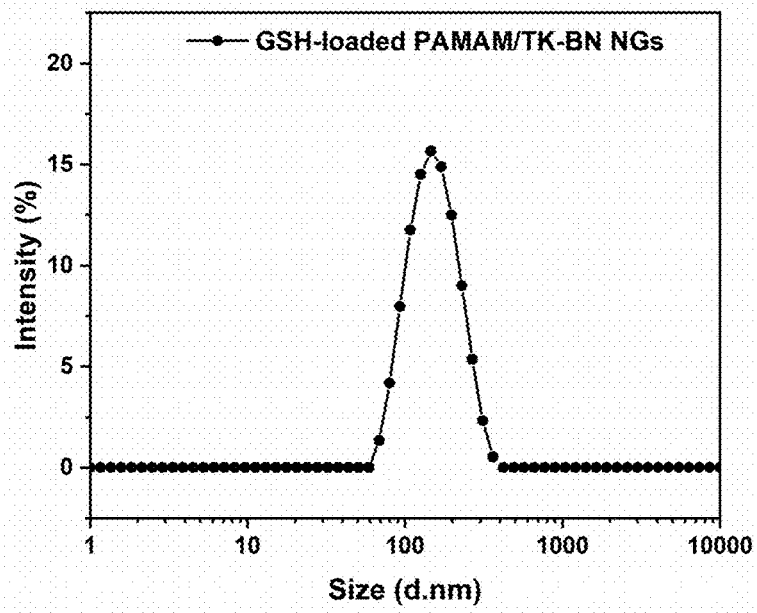
FIG. 6B is graph showing the average hydrodynamic size distribution data determined by DLS for the drug-loaded PAMAM/TK-BN nanogels formed in Example 6.

The same instruments described in Part 2 of Example 3 were used to physically characterize the GSH-loaded PAMAM/TK-BN NGs prepared in Part 1 of this Example. The size distribution of the GSH-loaded PAMAM/TK-BN NGs was also narrow, and the average hydrodynamic size determined by DLS slightly increased to 136 nm with a PDI of 0.129 (FIG. 6B). The zeta potential of the GSH-loaded PAMAM/TK-BN NGs decreased to 9.726±1.005 mV, which was due to neutralization caused by negative GSH.

Example 7

Fabrication of Plasmid-Loaded PAMAM/TK-BN NGs

1. Method

Figure 7A:
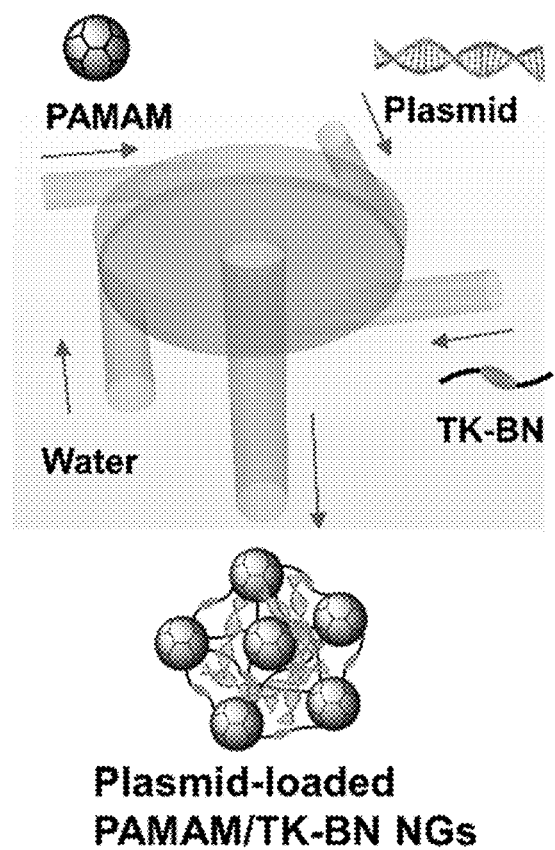
FIG. 7A is a schematic representation of a multi-inlet vortex mixer forming plasmid-loaded PAMAM/TK-BN nanogels (Example 7)

PAMAM G5 was dissolved in DNAase-free water by stirring at room temperature, forming a first solution having a concentration of 1 mg/mL. TK-BN was dissolved in acetone by mixing and shaking at room temperature, forming a second solution having a concentration of 0.75 mg/mL. In a DNAase-free container, plasmid was dissolved in DNAase-free water by mixing and shaking at room temperature, forming a third solution having a concentration of 0.2 mg/mL. These solutions were loaded into respective syringes, and the syringes were connected to respective inlets of the multi-inlet vortex mixer as shown in FIG. 7A. The fourth inlet was connected to a syringe containing DNAase-free water for injecting the solvent stream. Subsequently, these three solutions were mixed at an injection rate of 40 mL/min using the syringe pump. After being set for 1 minute, the received solution was rotary evaporated to remove acetone, yielding the plasmid-loaded PAMAM/TK-BN NGs.

2. Results

Figure 7B:
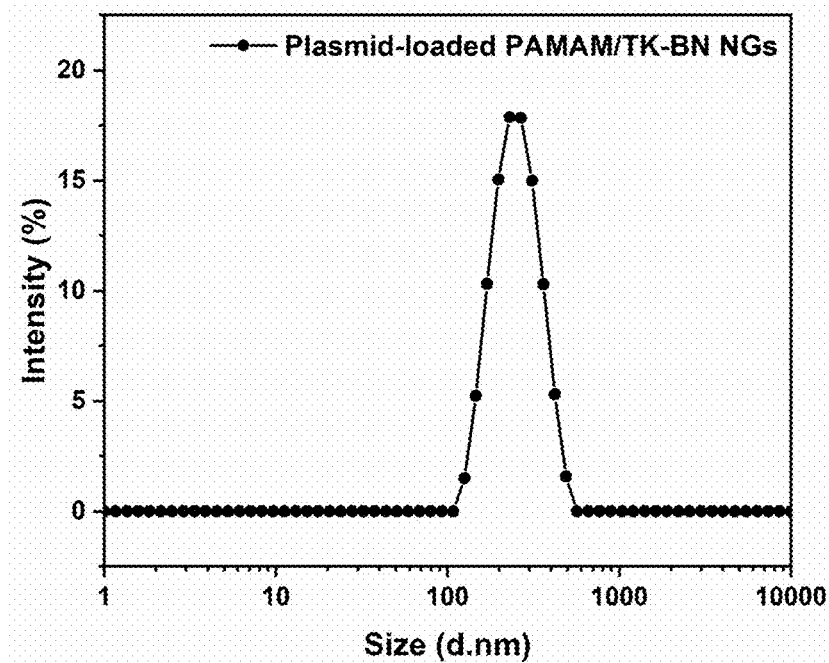
FIG. 7B is a graph showing the average hydrodynamic size distribution data determined by DLS for the plasmid-loaded PAMAM/TK-BN nanogels formed in Example 7.

The same instruments described in Part 2 of Example 3 were used to physically characterize the plasmid-loaded PAMAM/TK-BN NGs prepared in Part 1 of this Example. The size distribution of the plasmid-loaded PAMAM/TK-BN NGs was also narrow, and the average hydrodynamic size determined by DLS was 231 nm with a PDI of 0.174 (FIG. 7B). The zeta potential of the plasmid-loaded PAMAM/TK-BN NGs decreased to 10.14±0.388 mV, which was due to neutralization caused by negative plasmid.

Example 8

Fabrication of PAMAM-Cu/DSN NGs

1. Method

PAMAM-Cu was dissolved in water by stirring at room temperature, forming a first solution having a concentration of 1 mg/mL. Disulfide-NHS (DSN) linker was dissolved in acetone by mixing and shaking at room temperature, forming a second solution having a concentration of 0.5 mg/mL. The two solutions were loaded to syringes, and the syringe charged with PAMAM-Cu was connected to one inlet of the multi-inlet vortex mixer, while the syringe charged with DSN was connected to a second inlet. The remaining two inlets were connected to syringes with water. Subsequently, these solutions were mixed at an injection rate of 40 mL/min using the syringe pump. The received solution was set for 1 minute, yielding the PAMAM-Cu/DSN NGs.

2. Results

The size distribution and TEM instruments described in Part 2 of Example 3 were used to physically characterize the PAMAM-Cu/DSN NGs prepared in Part 1 of this Example. In addition, using a FEI Quanta 600F Environmental SEM equipped with a Bruker EDS system (Field Electron and Ion Company, FEI, Hillsboro, Oregon) instrument, energy-dispersive X-ray spectroscopy was used to obtain elemental mapping images (Cu, C, and O) and an integrated EDX spectrum image.

Figure 8A:
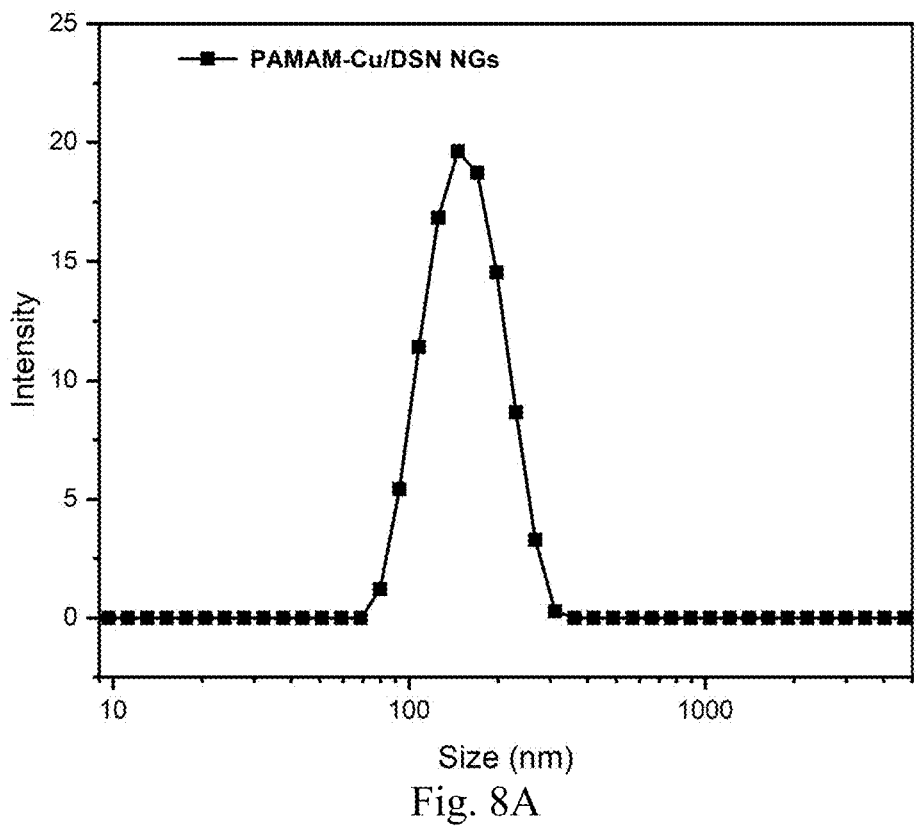
FIG. 8A is a graph showing the average hydrodynamic size distribution data determined by DLS for PAMAM-Cu/DSN nanogels (Example 8) formed according to one aspect of the invention.
Figure 8B:
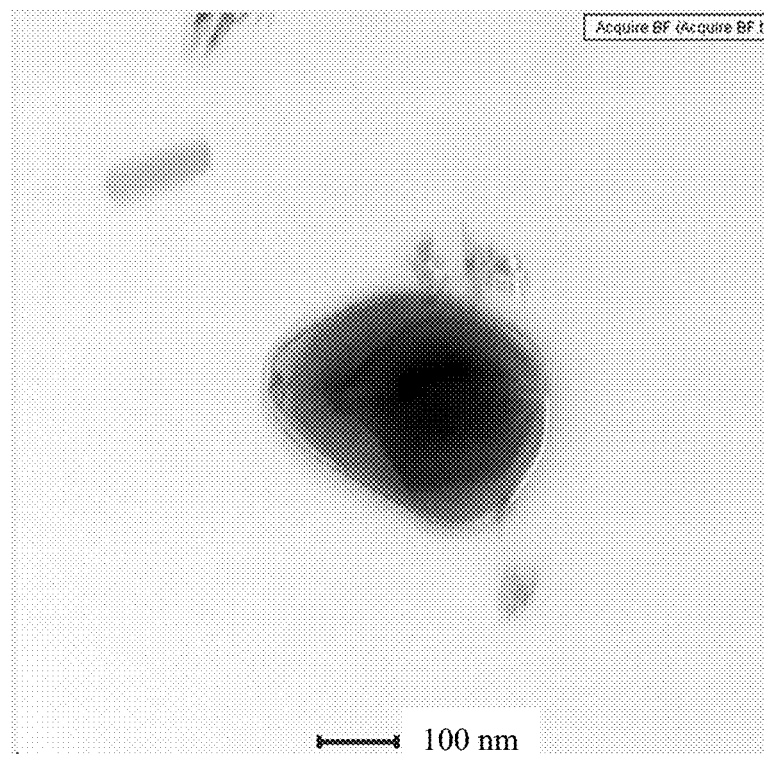
FIG. 8B is an SEM photograph of the PAMAM/TK-BN nanogels formed as described in Example 8.
Figure 8C:
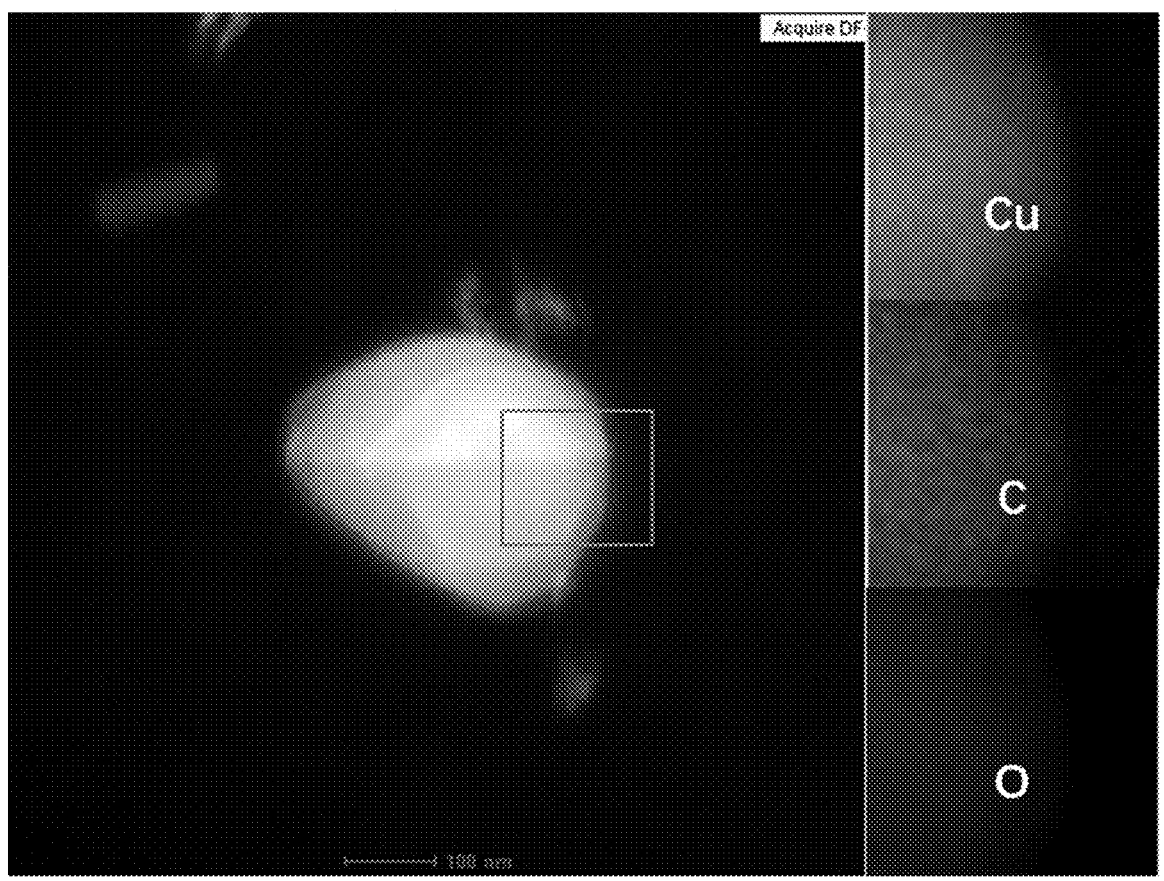
FIG. 8C is an energy-dispersive X-ray spectroscopy photograph of the PAMAM-Cu/DSN nanogels formed in Example 8.
Figure 8D:
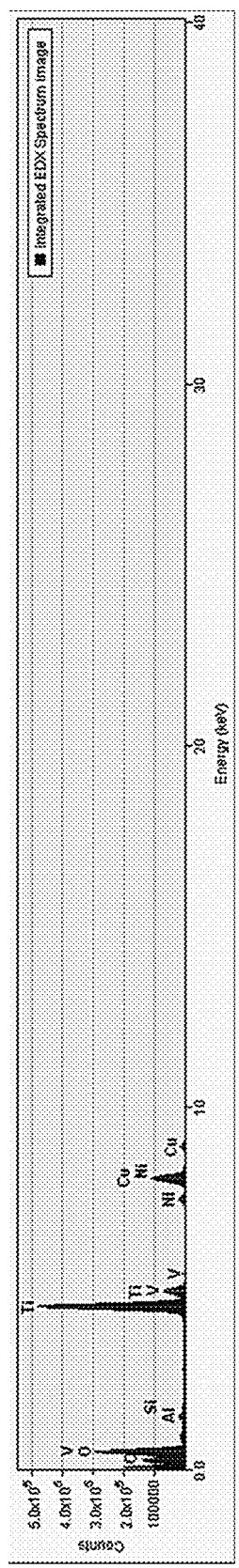
FIG. 8D is an integrated EDX spectrum image photograph of the PAMAM-Cu/DSN nanogels formed in Example 8.

The size distribution of the PAMAM-Cu/DSN NGs was narrow (FIG. 8A). The TEM image showed the morphology of the NGs (FIG. 8B). The element mapping (FIG. 8C) proved that the copper was successfully integrated into the NGs. FIG. 8D shows the integrated EDX spectrum image.

Example 9

Reynolds Number and Residence Time

Outlet volume flow at different pump rates was measured in order to determine the Reynolds number (Re) and Residence Time (RT) of the multi-inlet vortex mixer used in the above Examples. The procedures are described in Liu et al., Mixing in a multi-inlet vortex mixer (MIVM) for flash nano-precipitation, Chemical Engineering Science, Vol. 63, Issue 11, 2008, Pages 2829-2842, ISSN 0009-2509, https://doi.org/10.1016/j.ces.2007.10.020, incorporated by reference herein. Tables 4-6 provide Re and RT values.

TABLE 4

Chamber Re - Inlet Velocity Based

| Pump Flow Rate (mL/min) | Syringe Tube Velocity (m/s) | Mixer Inlet Velocity (m/s) | Single Inlet Re | Chamber Re |
|---|---|---|---|---|
| 10 | 0.000297 | 0.082893 | 827.03 | 3308.12 |
| 20 | 0.000595 | 0.165786 | 1654.06 | 6616.24 |
| 30 | 0.000893 | 0.248679 | 2481.09 | 9924.36 |
| 40 | 0.001191 | 0.331572 | 3308.12 | 13232.48 |
| 50 | 0.001488 | 0.414465 | 4135.15 | 16540.59 |

TABLE 5

Chamber Re - Outlet Velocity Based

| Pump Flow Rate (mL/min) | Syringe Tube Velocity (m/s) | Mixer Outlet Velocity (m/s) | Single Outlet <Re> | Chamber <Re> |
|---|---|---|---|---|
| 10 | 0.000297 | 0.336877 +/− 0.019 | 539.01 | 3368.78 |
| 20 | 0.000595 | 0.679724 +/− 0.006 | 1087.56 | 6797.24 |
| 30 | 0.000893 | 0.937190 +/− 0.036 | 1499.51 | 9371.91 |
| 40 | 0.001191 | 1.165975 +/− 0.076 | 1865.56 | 11659.76 |
| 50 | 0.001488 | 1.316509 +/− 0.062 | 2106.42 | 13165.11 |

TABLE 6

Residence Time Distribution

| Pump Flow Rate (mL/min) | Residence Time (s) |
|---|---|
| 10 | 1.16 |
| 20 | 0.575 |
| 30 | 0.417 |
| 40 | 0.336 |
| 50 | 0.297 |

We claim:

1. A method of forming a loaded nanogel, the method comprising micromixing a polymer, a crosslinker, a target, and a solvent system in a multi-inlet vortex mixer until the loaded nanogel is formed, wherein:
said polymer is chosen from polyamidoamine dendrimers, metal-decorated polyamidoamine dendrimers, polyethylenimine, chitosan, chitosan derivatives, amine-functionalized multi-armed polyethylene glycol, N-hydroxysuccinimide functionalized hyaluronic acid, sulfo-N-hydroxysuccinimide functionalized hyaluronic acid, N-hydroxysuccinimide functionalized multi-armed polyethylene glycol, sulfo-N-hydroxysuccinimide functionalized multi-armed polyethylene glycol, N-hydroxysuccinimide functionalized polyacrylic acid, sulfo-N-hydroxysuccinimide functionalized polyacrylic acid, or combinations thereof;

said crosslinker is chosen from bis-(N-hydroxysuccinimide) functionalized polyethylene glycols, bis-amine functionalized polyethylene glycols, bis-(N-hydroxysuccinimide) functionalized thioketal, disulfide (N-hydroxysuccinimide), cysteamine, 3,3'-dithiodipropionic acid di(N-hydroxysuccinimide ester), cis-aconitic anhydride functionalized polyethylene glycol, or combinations thereof; and said target is chosen from drugs, genes, proteins, plasmids, targeting ligands, or combinations thereof.

2. The method of claim 1, wherein said micromixing comprises creating a vortex of said polymer, crosslinker, target, and solvent system.

3. The method of claim 1, wherein said multi-inlet vortex mixer comprises at least three inlets operably connected to a mixing chamber, and further comprising, prior to said micromixing, introducing each of said polymer, crosslinker, and target into different inlets so that said polymer, crosslinker, and target flow to said mixing chamber.

4. The method of claim 3, wherein each of said polymer, crosslinker, and target is separately dispersed or dissolved in respective solvents so as to form a polymer stream, crosslinker stream, and target stream that are introduced into the different inlets, wherein said solvent system comprises said solvents.

5. The method of claim 4, further comprising introducing a solvent into a fourth inlet to create a solvent stream that flows to said mixing chamber.

6. The method of claim 1, wherein said solvent system comprises at least about 98% by weight water, based on the total weight of the solvent system taken as 100% by weight.

7. The method of claim 1, wherein said solvent system comprises less than about 5% by weight organic solvents other than acetone, based on the total weight of the solvent system taken as 100% by weight.

8. The method of claim 1, wherein said polymer comprises recurring units that comprise at least one reactive group chosen from one or more of N-hydroxysuccinimide, sulfo-N-hydroxysuccinimide, —NH$_2$, —NH—, thiol, methyl acrylate, methyl methacrylate, azide, alkyne, or combinations thereof.

9. The method of claim 1, wherein said polymer comprises recurring units that comprise a reactive group, and said crosslinker comprises a functional group that will covalently react with said reactive group.

10. The method of claim 4, wherein each of said polymer stream, crosslinker stream, and target stream are introduced at respective concentrations of about 0.1 mg/mL of solvent to about 100 mg/mL of solvent.

11. The method of claim 4, wherein each of said polymer stream, crosslinker stream, and target stream are introduced at respective rates of about 1 mL/min to about 100 mL/min.

12. The method of claim 1, wherein said loaded nanogel comprises a crosslinked polymer network with said target interspersed among said crosslinked polymer network.

* * * * *